(12) United States Patent
Cremer et al.

(10) Patent No.: US 12,193,717 B2
(45) Date of Patent: Jan. 14, 2025

(54) HYBRID BONE PLATES AND RELATED SYSTEMS AND METHODS

(71) Applicant: GLW, Inc., Englewood Cliffs, NJ (US)

(72) Inventors: Axel Cremer, Fahrenkrug (DE); Garret Mauldin, Erie, CO (US); Anna Zastrozna, Teaneck, NJ (US)

(73) Assignee: GLW, Inc., Englewood Cliffs, NJ (US)

( * ) Notice: Subject to any disclaimer, the term of this patent is extended or adjusted under 35 U.S.C. 154(b) by 460 days.

(21) Appl. No.: 17/716,479

(22) Filed: Apr. 8, 2022

(65) Prior Publication Data
US 2022/0323126 A1    Oct. 13, 2022

Related U.S. Application Data

(60) Provisional application No. 63/172,841, filed on Apr. 9, 2021.

(51) Int. Cl.
*A61B 17/80* (2006.01)
*A61L 31/02* (2006.01)
*A61L 31/06* (2006.01)

(52) U.S. Cl.
CPC ........ *A61B 17/8052* (2013.01); *A61L 31/022* (2013.01); *A61L 31/06* (2013.01)

(58) Field of Classification Search
CPC .... A61B 17/8052; A61L 31/022; A61L 31/06
See application file for complete search history.

(56) References Cited

U.S. PATENT DOCUMENTS

| | | | |
|---|---|---|---|
| 4,280,233 A | | 7/1981 | Raab |
| 4,338,926 A | * | 7/1982 | Kummer ............ A61B 17/8028 606/62 |
| 5,571,139 A | | 11/1996 | Jenkins, Jr. |
| 7,033,398 B2 | | 4/2006 | Graham |
| 7,850,690 B2 | | 12/2010 | Frigg et al. |

(Continued)

FOREIGN PATENT DOCUMENTS

| | | |
|---|---|---|
| CN | 101128157 | 2/2008 |
| CN | 101426444 | 5/2009 |

(Continued)

OTHER PUBLICATIONS

PCT International Search Report and Written Opinion, Application No. PCT/US2022/024025, dated Jul. 15, 2022.

(Continued)

*Primary Examiner* — Kevin T Truong
*Assistant Examiner* — Diana Jones
(74) *Attorney, Agent, or Firm* — MacMillan, Sobanski & Todd, LLC

(57) ABSTRACT

A bone plate includes a main body defining one or more openings and a cavity. A support member formed of a different material than the material of the main body is disposed in the cavity and defines one or more openings, each of which is coaxial with an opening of the main body. The support member extends into circumferential recesses defined by the main body. Circumferential projections bounding each main body opening are disposed between circumferential projections of the main body and are disposed entirely within the support member. Bone plate systems, methods of treatment, and methods of manufacturing are also described.

20 Claims, 9 Drawing Sheets

(56) References Cited

U.S. PATENT DOCUMENTS

| | | |
|---|---|---|
| 8,092,505 B2 | 1/2012 | Sommers |
| 8,147,530 B2 | 4/2012 | Strnad et al. |
| 8,454,606 B2 | 6/2013 | Frigg et al. |
| 8,663,224 B2 | 3/2014 | Overes et al. |
| 8,702,767 B2 | 4/2014 | Nebosky et al. |
| 8,709,055 B2 | 4/2014 | Beyar |
| 8,784,430 B2 | 7/2014 | Kay et al. |
| 8,979,865 B2 | 3/2015 | Fan et al. |
| 8,998,987 B2 | 4/2015 | Wallick |
| 9,101,417 B2 | 8/2015 | Beyar et al. |
| 9,174,390 B2 | 11/2015 | Lechmann et al. |
| 9,259,255 B2 | 2/2016 | Lewis et al. |
| 9,440,379 B2 | 9/2016 | Smith et al. |
| 9,452,001 B2 | 9/2016 | Faccioli et al. |
| 9,492,210 B2 | 11/2016 | Rains et al. |
| 9,730,742 B2 | 8/2017 | Lewis et al. |
| 9,770,273 B2 | 9/2017 | Guitelman |
| 10,022,164 B2 | 7/2018 | Mangiardi |
| 10,022,165 B2 | 7/2018 | Mangiardi |
| 10,028,777 B2 | 7/2018 | Beyar et al. |
| 10,561,456 B2 | 2/2020 | Cawley et al. |
| 2006/0247638 A1 | 11/2006 | Trieu et al. |
| 2007/0049938 A1 | 3/2007 | Wallace et al. |
| 2007/0049939 A1 | 3/2007 | Wallace et al. |
| 2007/0049940 A1 | 3/2007 | Wallace et al. |
| 2007/0233071 A1 | 10/2007 | Dewey et al. |
| 2009/0018590 A1 | 1/2009 | Dorawa et al. |
| 2009/0043307 A1 | 2/2009 | Faccioli et al. |
| 2009/0248087 A1 | 10/2009 | Lewis et al. |
| 2009/0299369 A1* | 12/2009 | Orbay ................. A61B 17/80 606/70 |
| 2010/0114097 A1 | 5/2010 | Siravo et al. |
| 2010/0211118 A1 | 8/2010 | Christen et al. |
| 2011/0015682 A1 | 1/2011 | Lewis et al. |
| 2011/0093020 A1 | 4/2011 | Wu |
| 2011/0208189 A1 | 8/2011 | Faccioli et al. |
| 2011/0218570 A1* | 9/2011 | Felix ................. A61B 17/80 606/280 |
| 2011/0245832 A1 | 10/2011 | Giersch et al. |
| 2012/0271361 A1 | 10/2012 | Zhou et al. |
| 2014/0105776 A1 | 4/2014 | Ellero et al. |
| 2014/0188113 A1 | 7/2014 | Overes et al. |
| 2017/0105776 A1 | 4/2017 | Lutz |
| 2018/0168811 A1 | 6/2018 | Ranganathan et al. |
| 2019/0053836 A1 | 2/2019 | Sweeney et al. |
| 2019/0216513 A1 | 7/2019 | Sands et al. |

FOREIGN PATENT DOCUMENTS

| | | |
|---|---|---|
| CN | 101686844 | 3/2010 |
| CN | 102355863 | 2/2012 |
| CN | 102008751 | 1/2014 |
| DE | 102013013138 | 9/2014 |
| EP | 1265653 | 6/2004 |
| GB | 2405342 | 3/2005 |
| JP | H07213534 | 8/1995 |
| WO | 0174262 | 10/2001 |
| WO | 2004024012 | 3/2004 |
| WO | 2007101267 | 9/2007 |
| WO | 2008134264 | 11/2008 |
| WO | 2011066522 | 6/2011 |
| WO | 2011082152 | 7/2011 |
| WO | 2012065068 | 5/2012 |
| WO | 2014015262 | 1/2014 |
| WO | 2015137911 | 9/2015 |
| WO | 2015172842 | 11/2015 |
| WO | 2016125054 | 8/2016 |
| WO | 2018013594 | 1/2018 |
| WO | 2020191009 A1 | 9/2020 |

OTHER PUBLICATIONS

PCT Search Report and Written Opinion, Application No. PCT/US2020/023280, dated Aug. 18, 2020.

* cited by examiner

HYBRID BONE PLATES AND RELATED SYSTEMS AND METHODS

RELATED APPLICATION

This application claims priority to U.S. Provisional Application No. 63/172,841, filed Apr. 9, 2021. The entire contents of this related application are hereby incorporated by reference into this disclosure.

FIELD

The disclosure relates to the field of medical devices. More particularly, the disclosure relates to the field of orthopedic medical devices. Specific examples relate to bone plates for internal fixation of fractures. The disclosure also relates to bone plate systems, methods of treatment, and methods of manufacturing.

BACKGROUND

Bone plates have been widely used for internal fixation of fractures for years. Indeed, various bone plate structures are known in the art. For example, some conventional bone plates are constructed from either metal, such as titanium alloys and stainless steel, or polymers, such as carbon fiber or polyethertherketone ("PEEK").

While conventional bone plates are widely used, they do have several drawbacks. For example, while metal plates typically demonstrate adequate wear resistance and strength, conventional solid metal construction hinders a user's ability to visualize the fracture site while using X-ray imaging techniques and equipment. Titanium plates often require the use of a computed tomography (CT) scan to image a fracture site when assessing healing of the bone, which exposes a patient to a higher level of radiation than that involved in a standard X-ray. Moreover, while carbon fiber and PEEK bone plates provide an option for increased visibility of the fracture site using standard X-ray imaging, these plates must be significantly thicker than metal bone plates to achieve desirable strength. Furthermore, PEEK bone plates can also be entirely transparent, which creates additional challenges when attempting to visualize the position of the plate in post-operative evaluations.

A need exists, therefore, for improved bone plates, methods of treatment, and methods of manufacturing bone plates.

BRIEF SUMMARY OF SELECTED EXAMPLES

Various example bone plates are described herein.

An example bone plate includes a main body having first and second opposing surfaces. The main body defines a circumferential wall that at least partially bounds a passageway extending from the first surface to the second surface. The main body includes a non-porous portion and a porous portion. The circumferential wall is at least partially formed by the porous portion.

Another example bone plate includes a main body having first and second opposing surfaces. The main body defines a circumferential wall that at least partially bounds a passageway extending from the first surface to the second surface. The main body includes a non-porous portion and a porous portion. The circumferential wall is cooperatively formed by the non-porous portion and the porous portion.

Another example bone plate includes a main body having first and second opposing surfaces. The main body defines a circumferential wall that at least partially bounds a passageway extending from the first surface to the second surface. The main body includes a non-porous portion, a first porous portion, and a second porous portion. The circumferential wall is at least partially formed by the first porous portion and the second surface is at least partially formed by the second porous portion.

Various bone plate systems are also described.

An example bone plate system comprises a bone plate according to an embodiment, such as the examples described and illustrated herein, and a plurality of bone screws.

Various methods of treatment are also described.

An example method of treatment comprises placing a bone plate according to an embodiment across a fracture in a bone such that the lower surface of the bone plate is in contact with the bone. A second step comprises driving a bone screw through a passageway of the bone plate such that the thread of the bone screw deforms the porous portion of the bone plate that comprises a portion of the circumferential wall of the passageway to form a mating thread in the circumferential wall. The second step can be repeated a suitable number of times until a bone screw is driven through each passageway of the bone plate and into the bone.

Various methods of manufacturing a bone plate are also described.

An example method of manufacturing comprises forming a main body having a porous portion and a non-porous portion such that the main body defines a plurality of passageways, each of which is bounded at least partially by the porous portion.

Another example method of manufacturing a bone plate comprises 3D printing a main body having a porous portion and a non-porous portion such that the main body defines a plurality of passageways, each of which is bounded at least partially by the porous portion, and a cavity. Another step comprises disposing a support member in the cavity. In one example method, this is accomplished by injection molding the support member into the cavity such that the polymeric material of the support member extends into the passageways of the porous portion of the main body that bounds each of the passageways. In another example, this is accomplished by 3D printing the support member onto the main body such that the support member abuts the porous portion of the main body that bounds each of the passageways. In this example, the support member can be formed to include its own porous portion, such as a porous portion that forms a part of the lower surface of the bone plate that will contact the bone when placed across a fracture in the bone. In another example, this is accomplished by 3D printing the support member simultaneously with the 3D printing of the main body. In this example, the support member can be formed to include its own porous portion, such as a porous portion that forms a part of the lower surface of the bone plate that will contact the bone when placed across a fracture in the bone.

Additional understanding of the inventive bone plates, bone plate systems, methods of treatment, and methods of manufacturing can be obtained by reviewing the detailed description of selected examples, below, with reference to the appended drawings.

DETAILED DESCRIPTION OF SELECTED EXAMPLES

The following detailed description and the appended drawings describe and illustrate various example bone plates, bone plate systems, methods of treatment, and methods of manufacturing a bone plate. The description and drawings are provided to enable one skilled in the art to make and use one or more example bone plates and bone plate systems, and to perform one or more example methods of treatment and methods of manufacturing a bone plate. They are not intended to limit the scope of the claims in any manner.

As used herein, the term "porous," and grammatically related terms, refers to a macro structural configuration of a component or portion of a component in which the material of the component or portion of a component defines a series of passageways into which material, such as a liquid, can enter. The passageways can be randomly distributed throughout the component or portion of a component, or can be distributed throughout the component or portion of a component in an ordered fashion. As an example, a lattice structure created during 3D printing of a metal component or portion of a metal component provides a porous structure consistent with this definition of "porous." The term does not include micro structural pores that naturally occur in the material that comprises the component or portion of a component.

As used herein, the term "non-porous," and grammatically related terms, refers to a macro structural configuration of a component or portion of a component in which the material of the component or portion of a component does not define a series of passageways into which material, such as a liquid, can enter.

Figure 1:
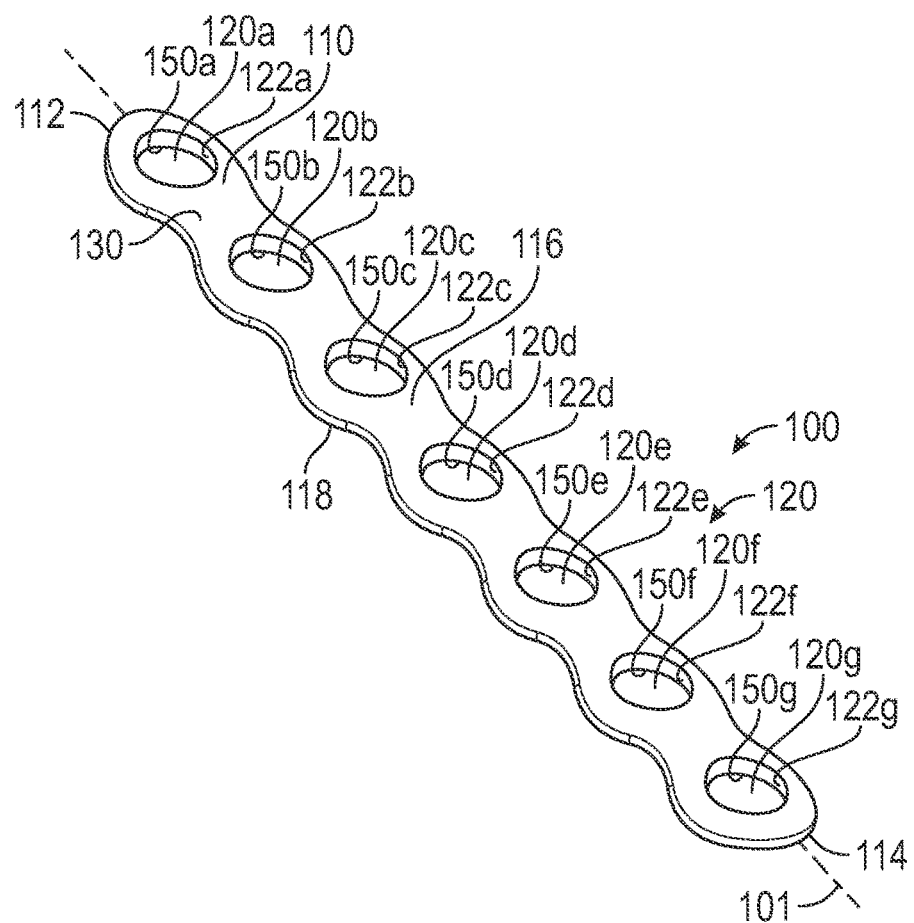
FIG. 1 is a perspective view of an example bone plate.
Figure 2:
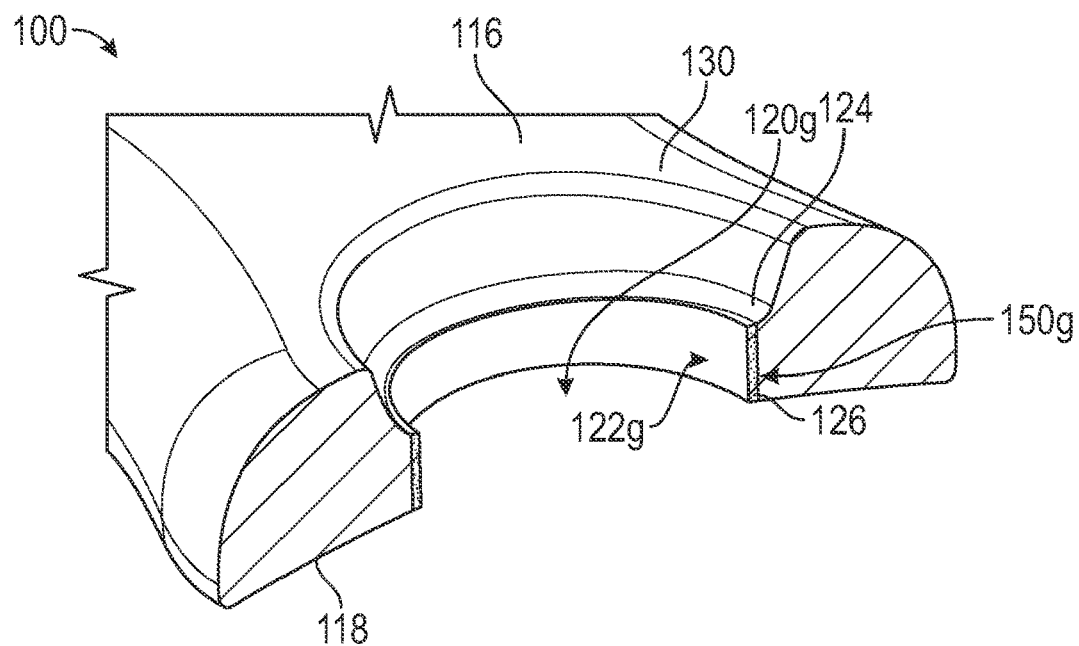
FIG. 2 is a partial perspective view, partially broken away, of the bone plate illustrated in FIG. 1.
Figure 3:
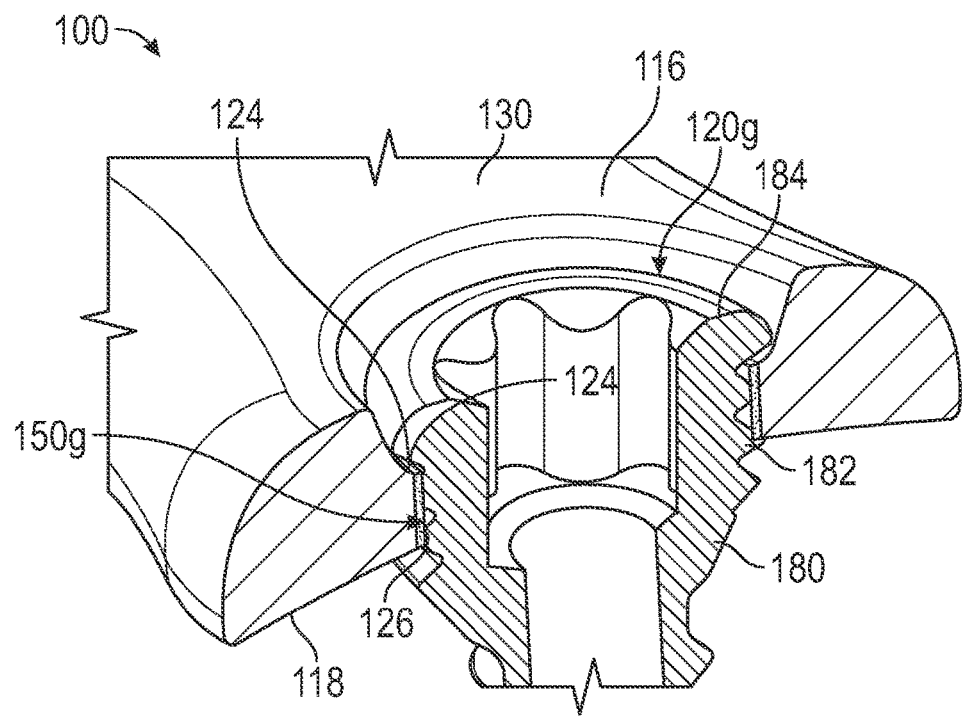
FIG. 3 is a partial perspective view, partially broken away, of the bone plate illustrated in FIG. 1 with a bone screw positioned within the opening of the bone plate.

FIGS. 1, 2 and 3 illustrate an example bone plate 100. The bone plate 100 has a main body 110 having a first end 112, a second end 114, and a lengthwise axis 101 extending between the first end 112 and the second end 114. The main body 110 has first 116 and second 118 opposing surfaces, and defines a plurality of passageways 120. Each passageway 120a, 120b, 120c, 120d, 120e, 120f, 120g of the plurality of passageways 120 extends through the entire thickness of the main body 110, from the first surface 116 to the second surface 118. As such, each passageway 120a, 120b, 120c, 120d, 120e, 120f, 120g provides a through opening within which another component can be disposed, such as a bone screw useful in securing the bone plate 100 across a fracture in a bone as part of a fixation procedure.

The main body 110 defines a circumferential wall 122a, 122b, 122c, 122d, 122e, 122f, 122g for each passageway 120a, 120b, 120c, 120d, 120e, 120f, 120g of the plurality of passageways 120. Each circumferential wall 122a, 122b, 122c, 122d, 122e, 122f, 122g bounds a respective passageway 120a, 120b, 120c, 120d, 120e, 120f, 120g.

The main body 110 includes a non-porous portion 130 and a porous portion 150. In the illustrated example, the non-porous portion 130 is a continuous portion of the main body 110, while the porous portion 150 comprises a plurality of discrete porous portions 150a, 150b, 150c, 150d, 150e, 150f, 150g. Each circumferential wall 122a, 122b, 122c, 122d, 122e, 122f, 122g is cooperatively formed by the non-porous portion 130 and one of the discrete porous portions 150a, 150b, 150c, 150d, 150e, 150f, 150g. As best illustrated in FIGS. 2 and 3, circumferential wall 122g is recessed within passageway 120g, providing a countersink structure for screw 180. Non-porous portion 130 of the main body 110 defines the upper portion 124 of the circumferential wall 122g, while porous portion 150g defines the lower portion 126 of the circumferential wall 122g. The lower portion 126 forms a part of the lower surface 118 of the main body 110. Thus, in this embodiment, lower surface 118 is cooperatively formed by the non-porous portion 130 and the porous portion 150, via discrete porous portions 150a, 150b, 150c, 150d, 150e, 150f, 150g.

This structural configuration of the circumferential wall 122g is considered advantageous at least because it positions the porous portion 150g of the circumferential wall 122g beneath the non-porous portion 130 of the circumferential wall 122g with respect to the opposing surfaces 116, 118. As best illustrated in FIG. 3, with respect to passageway 120g, this enables the thread 182 of screw 180 to deform the structure of the porous portion 150g as the screw 180 is driven into the passageway 120g, effectively forming a thread in the porous portion 150g that mates with the thread 182 of the screw 180. The non-porous portion 130 ensures that the head 184 of the screw 180 does not pass through the opening, as the non-porous portion 130 will resist the deformation that the porous portion 150g permits.

In the illustrated example, each circumferential wall 122a, 122b, 122c, 122d, 122e, 122f, 122g has a similar structure to that described above for circumferential wall 122g, with porous portion 150a, 150b, 150c, 150d, 150e, 150f, 150g beneath the non-porous portion 130 with respect to the opposing surfaces 116, 118. It is noted, though, that bone plates according to other examples can include circumferential walls having different structures. For example, it may be desirable to include one or more circumferential walls having a thread that is fully formed by the non-porous portion of a bone plate according to an embodiment in addition to a circumferential wall having the structural configuration described above. Inclusion of such a circumferential ensures that at least one thread is available that does not require thread forming action by a screw during placement of the bone plate, which may be desirable. Inclusion of at least one circumferential wall having the structural configuration described and illustrated above is considered advantageous at least because it ensures that at least one screw will be installed with thread forming action, providing desirable securement and bony ingrowth properties for the bone plate.

A bone plate according to an embodiment can include any suitable number of passageways. A skilled artisan will be able to select an appropriate number of passageways for a bone plate according to a particular embodiment based on various considerations, including the anatomical location at which the bone plate is intended to be used. The inclusion of seven passageways in the bone plate 100 illustrated in FIGS. 1 through 3 is merely an example of a suitable number of passageways. Similarly, a bone plate according to an embodiment can have any suitable overall shape. A skilled artisan will be able to select an appropriate shape for a bone plate according to a particular embodiment based on various considerations, including the anatomical location at which the bone plate is intended to be used. The elongate strip shape of the bone plate 100 illustrated in FIGS. 1 through 3 is merely an example of a suitable overall shape.

The porous portion in a bone plate according to a particular embodiment can have any suitable dimensions, and a skilled artisan will be able to select appropriate dimensions for a porous portion in a bone plate according to a particular embodiment based on various considerations, including the function of the porous portion. For example, in embodiments in which the porous portion forms a portion of the circumferential wall bounding a screw passageway and is to deform in response to a screw being driven through the passageway, the inventors have determined that a porous portion having a thickness of between about 1 mm and 2 mm is suitable for a passageway having an inner diameter of 4 mm. In embodiments in which the porous portion forms a boundary for a cavity into which a support member is to be formed, such as by injection molding, the inventors have determined that a porous portion having a thickness of between about 0.5 mm and 1 mm is suitable.

Figure 4:
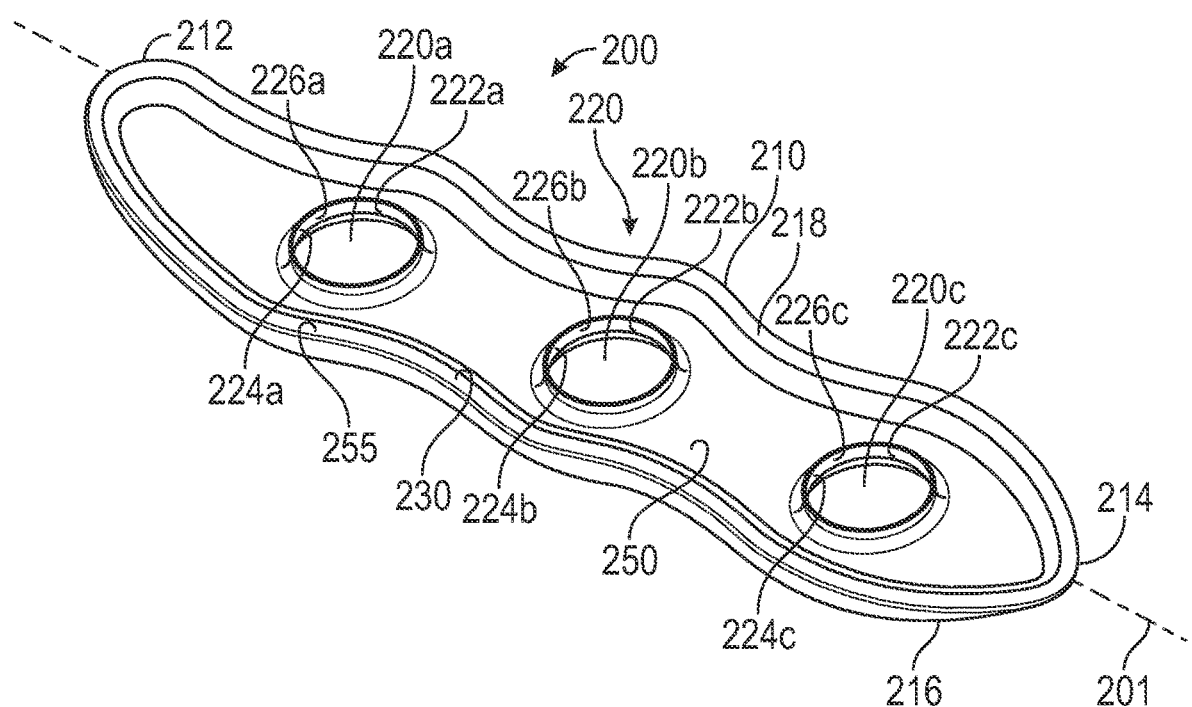
FIG. 4 is a partial perspective view of another example bone plate.

FIG. 4 illustrates another example bone plate 200. The bone plate 200 is similar to the bone plate 100 illustrated in FIGS. 1 through 3 and described above, except as detailed below. Thus, bone plate 200 has a main body 210 having a first end 212, a second end 214, and a lengthwise axis 201 extending between the first end 212 and the second end 214. The main body 210 has first 216 and second 218 opposing surfaces, and defines a plurality of passageways 220. For illustrative purposes only, the bone plate 200 is positioned in the opposite orientation of the bone plate 100 in FIGS. 1 through 3, such that the second surface 218 is upright and the first surface 216 is downward. Each passageway 220a, 220b, 220c of the plurality of passageways 220 extends through the entire thickness of the main body 210, from the first surface 216 to the second surface 218. As such, each passageway 220a, 220b, 220c provides a through opening within which another component can be disposed, such as a bone screw useful in securing the bone plate 200 across a fracture in a bone as part of a fixation procedure.

The main body 210 defines a circumferential wall 222a, 222b, 222c for each passageway 220a, 220b, 220c of the plurality of passageways 220. Each circumferential wall 222a, 222b, 222c bounds a respective passageway 220a, 220b, 220c.

The main body 210 includes a non-porous portion 230 and a porous portion 250. The non-porous portion 230 is a continuous portion of the main body 210. In this example, and in contrast to first example bone plate 100, porous portion 250 is also a continuous portion of the main body 210. Each circumferential wall 222a, 222b, 222c is cooperatively formed by the non-porous portion 230 and the porous portion 250. Each circumferential wall 222a, 222b, 222c is recessed within a respective passageway 220a, 220b, 220c, providing a countersink structure for a bone screw. Non-porous portion 230 of the main body 210 defines the upper portion 224a, 224b, 224c of each circumferential wall 222a, 222b, 222c, while porous portion 250 defines the lower portion 226a, 226b, 226c of each circumferential wall 222a, 222b, 222c. The lower portion 226a, 226b, 226c of each circumferential wall 222a, 222b, 222c is continuous and flush with the lower surface 218 of the main body 210. Lower surface 218 is cooperatively formed by the non-porous portion 230 and the porous portion 250. In this example, non-porous portion 230 forms a perimeter edge 255 of the lower surface 218.

This structural configuration is considered advantageous at least because it provides the desirable thread forming capability of the porous portion 250 in the passageways while also positioning the porous portion 250 on the majority of the lower surface 218 of the main body 210, which is the bone-contacting surface of the bone plate 200. The porous structure of the porous portion 250 provides structure that is advantageous for bony ingrowth following securement of the bone plate 200 to a bone. Taken together, the thread forming capability provided by the porous portion 250 positioned within the passageways 220a, 220b, 220c and the advantageous bony ingrowth structure provided by the porous portion positioned on the majority of the lower surface 218, the porous portion 250 provides desirable securement properties for the bone plate 200.

The porous portion can comprise any suitable portion of the lower surface in a bone plate according to a particular embodiment, and a skilled artisan will be able to select a suitable portion, based on percentage of total surface area of the lower surface, for a bone plate according to a specific embodiment based on various considerations, including the anatomical location at which the bone plate is intended to be used. Examples of suitable percentages of total surface area of the lower surface that the porous portion comprises include, but are not limited to, at least about 50% of the total surface area of the lower surface, greater than 50% of the total surface area of the lower surface, between about 60% and about 90% of the total surface area of the lower surface, between about 70% and about 90% of the total surface area of the lower surface, between about 80% and about 90% of the total surface area of the lower surface, and between about 85% and about 90% of the total surface area of the lower surface.

While the bone plate illustrated in FIGS. 1 through 3 and the bone plate 200 illustrated in FIG. 4 are monolithic structures, bone plates according to some examples include multiple components. Indeed, hybrid bone plates, which include components of different materials, such as a metal component and a polymeric component, provide certain advantages, as described below.

Figure 5:
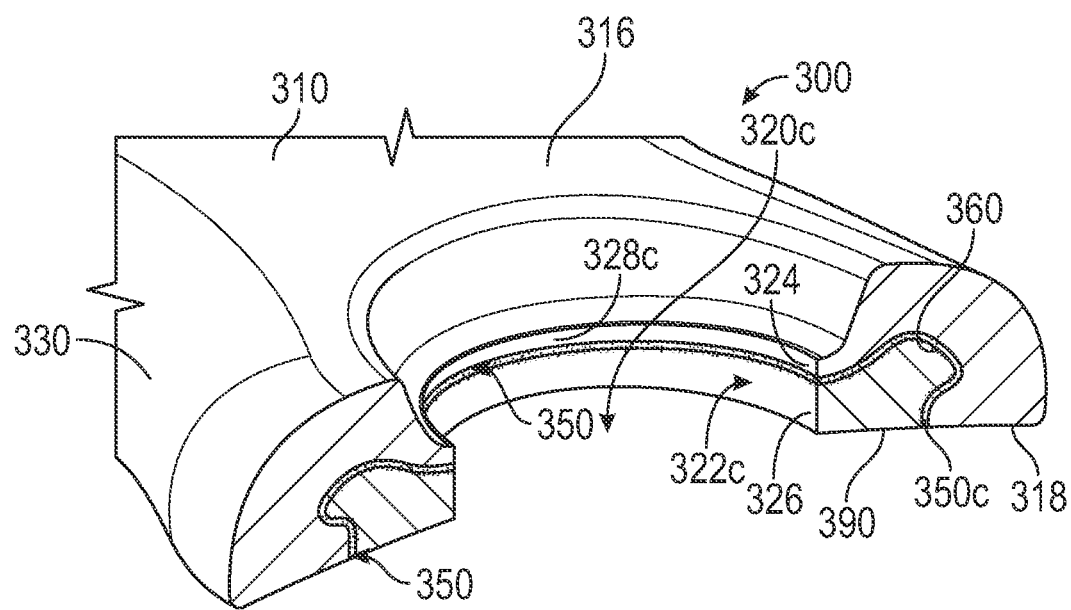
FIG. 5 is a partial perspective view, partially broken away, of another example bone plate.

FIG. 5 illustrates another example bone plate 300. Bone plate 300 has a main body 310 and a support member 390. Main body 310 defines a cavity 360 in which support member 390 is disposed.

Main body 310 has a first end 312, a second end 314, and a lengthwise axis 301 extending between the first end 312 and the second end 314. The main body 310 has first 316 and second 318 opposing surfaces. The main body 310 and support member 390 cooperatively define a plurality of passageways 320. Each passageway 320a, 320b, 320c of the plurality of passageways 320 extends through the entire thickness of the bone plate 300, from the first surface 316 to the second surface 318. As such, each passageway 320a, 320b, 320c provides a through opening within which another component can be disposed, such as a bone screw useful in securing the bone plate 300 across a fracture in a bone as part of a fixation procedure.

The main body 310 and support member 390 cooperatively define a circumferential wall 322a, 322b, 322c for each passageway 320a, 320b, 320c of the plurality of passageways 320. Each circumferential wall 322a, 322b, 322c bounds a respective passageway 320a, 320b, 320c.

The main body 310 includes a non-porous portion 330 and a porous portion 350. The non-porous portion 330 is a continuous portion of the main body 310 while the porous portion 350 comprises a plurality of discrete porous portions 350a, 350b, 350c. Each circumferential wall 322a, 322b, 322c is cooperatively formed by the non-porous portion 330, one of the discrete porous portions 350a, 350b, 350c, and the support member 390. Each circumferential wall 322a, 322b, 322c is recessed within a respective passageway 320a, 320b, 320c, providing a countersink structure for a bone screw. Non-porous portion 330 of the main body 310 defines the upper portion 324 of each circumferential wall 322c, while the support member 390 defines the lower portion 326 of the circumferential wall 322c. Porous portion 350c provides an intermediate 328c portion of the circumferential wall 322a. In this example, lower surface 318 is cooperatively formed by the non-porous portion 330 of the main body 310, the porous portions 350a, 350b, 350c of the main body 310, and the support member 390.

In this example, the porous portion 350 provides boundaries for the cavity 360 of the main body 310. This is particularly advantageous for bone plates in which the support member is formed by injection molding, as the porous portion 350 permits polymer to enter the passageways of the porous portion, enhancing fixation between the main body 310 and support member 390. Furthermore, positioning of the porous portion 350 in the circumferential walls 322a, 322b, 322c also provides the thread forming capability described above, providing additional advantage to this structural configuration.

Figure 6:
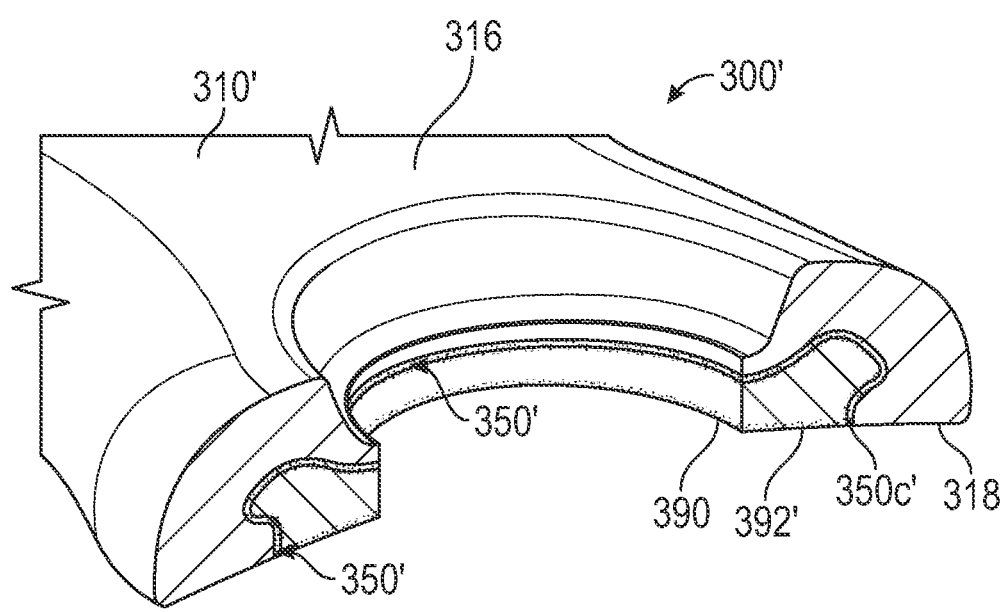
FIG. 6 is a partial perspective view, partially broken away, of another example bone plate.
Figure 7:
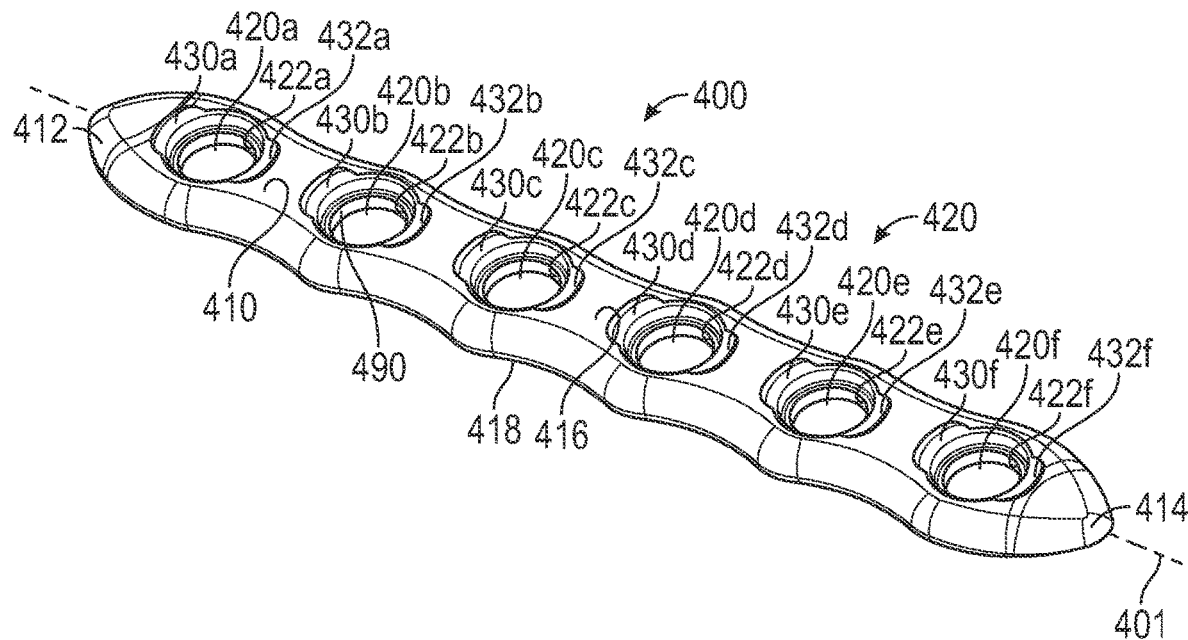
FIG. 7 is a perspective view of another example bone plate.

Alternatively, as illustrated in FIG. 6, the support member 390' can abut the porous portion 350' of the main body 310', such that the polymer of the support member 390' does not extend into the passageways of the porous portion 350'. Also alternatively, support member 390' can include a porous portion 392' as well. In this alternative example, porous portion 392' of the support member 390' forms a portion of lower surface 318', providing beneficial bony ingrowth properties for the bone plate 300'. This structural configuration is considered particularly advantageous for bone plates in which the support member is formed by 3D printing, either onto the main body or simultaneously with the main body.

Figure 8:
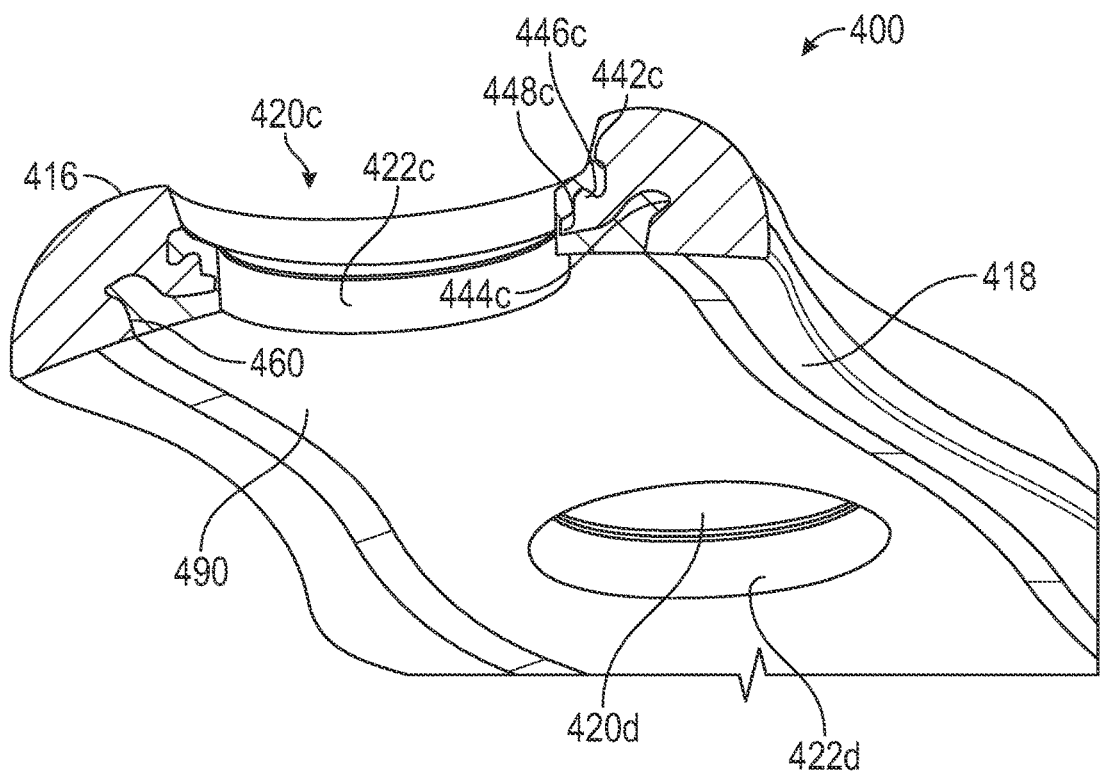
FIG. 8 is a partial perspective view, partially broken away, of the bone plate illustrated in FIG. 7.

FIGS. 7, 8, 9, 10, and 11 illustrate another example bone plate 400. The bone plate 400 is similar to the bone plate 300 illustrated in FIG. 5 and described above, except as detailed below. Thus, bone plate 400 has a main body 410 having a first end 412, a second end 414, and a lengthwise axis 401 extending between the first end 412 and the second end 414. The main body 410 has first 416 and second 418 opposing surfaces, and defines a plurality of passageways 420. Each passageway 420a, 420b, 420c, 420d, 420e, 420f of the plurality of passageways 420 extends through the entire thickness of the main body 410, from the first surface 416 to the second surface 418. As such, each passageway 420a, 420b, 420c, 420d, 420e, 420f provides a through opening within which another component can be disposed, such as a bone screw useful in securing the bone plate 400 across a fracture in a bone as part of a fixation procedure. Main body 410 defines a cavity 460 in which support member 490 is disposed. Support member 490 defines a circumferential wall 422a, 422b, 422c, 422d, 422e, 422f for each passageway 420a, 420b, 420c, 420d, 420e, 420f of the plurality of passageways 420. Each circumferential wall 422a, 422b, 422c, 422d, 422e, 422f bounds a respective passageway 420a, 420b, 420c, 420d, 420e, 420f. As best illustrated in FIG. 8, lower surface 418 is cooperatively formed by the main body 410 and the support member 490. Upper surface 416 of main body 410 defines first 430a and second 432a depressions disposed adjacent passageway 420a, first 430b and second 432b depressions disposed adjacent passageway 420b, first 430c and second 432c depressions disposed adjacent passageway 420c, first 430d and second 432d depressions disposed adjacent passageway 420d, first 430e and second 432e depressions disposed adjacent passageway 420e, and first 430f and second 432f depressions disposed adjacent passageway 420f.

Figure 9:
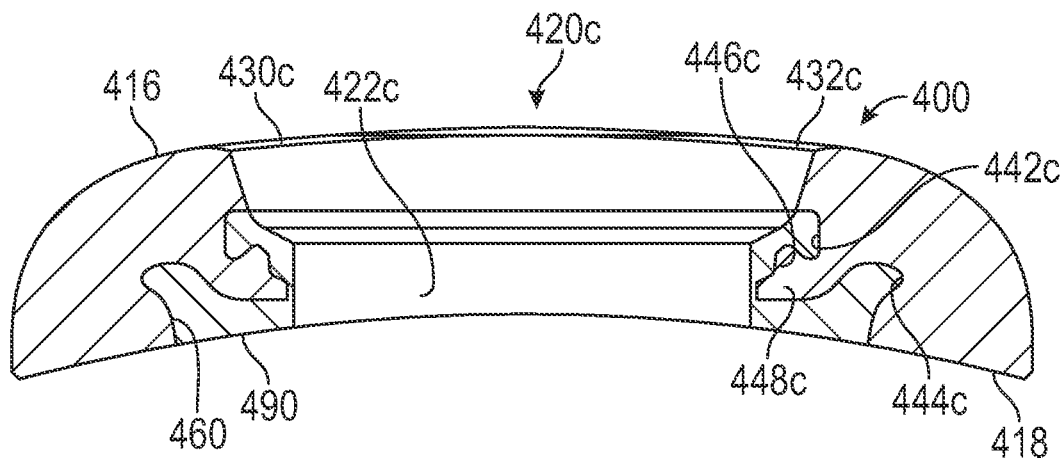
FIG. 9 is a sectional view of the bone plate illustrated in FIG. 7.

In this embodiment, main body 410 defines an upper circumferential recess and a lower circumferential recess around each passageway 420a, 420b, 420c, 420d, 420e, 420f of the plurality of passageways 420. FIGS. 8 and 9 illustrate the upper circumferential recess 442c and the lower circumferential recess 444c that are disposed around passageway 420c. In this example, an upper circumferential recess that is identical to upper circumferential recess 442c and a lower circumferential recess that is identical to lower circumferential recess 442d is disposed around each of the other passageways 420a, 420b, 420d, 420e, 420f defined by the main body 410, but are not visible in the drawings.

In the illustrated example, the upper circumferential recess 442c extends radially inward from the central axis of the passageway 420c and generally in an upward direction toward the upper surface 416 of the main body 410. The lower circumferential recess 444c also extends radially inward from the central axis of the passageway 420c and generally in an upward direction toward the upper surface 416 of the main body 410. The lower circumferential recess 444c extends further radially inward relative to the central axis of the passageway 420c than the upper circumferential recess 442c.

Figure 10:
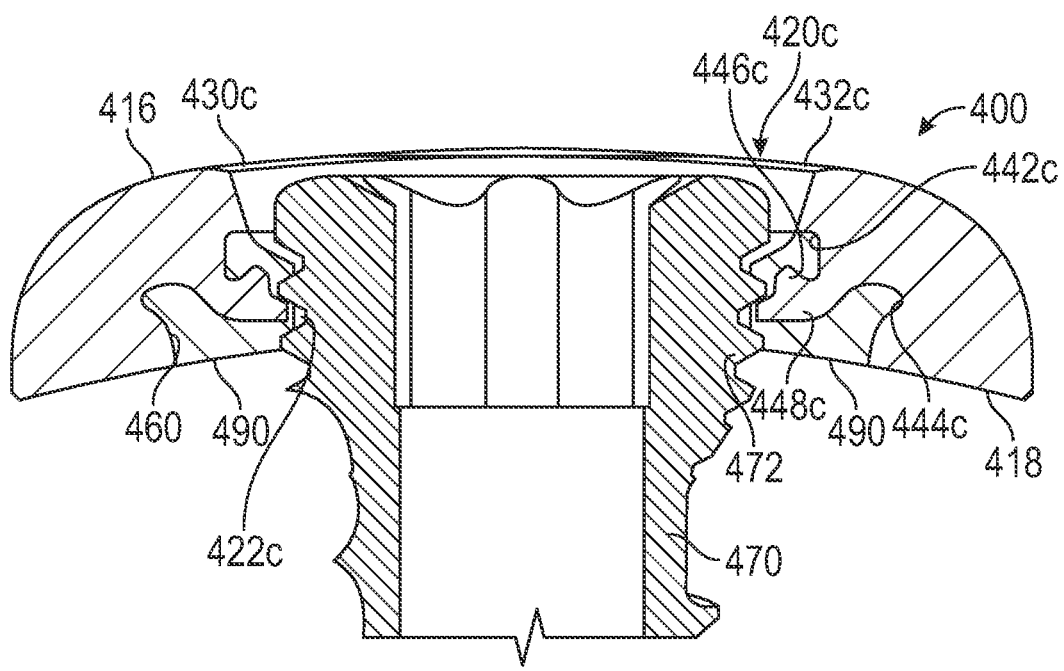
FIG. 10 is a sectional view of the bone plate illustrated in FIG. 7 with a bone screw positioned within an opening of the bone plate. The bone screw extends through the opening at a first angle relative to the central axis of the opening.
Figure 11:
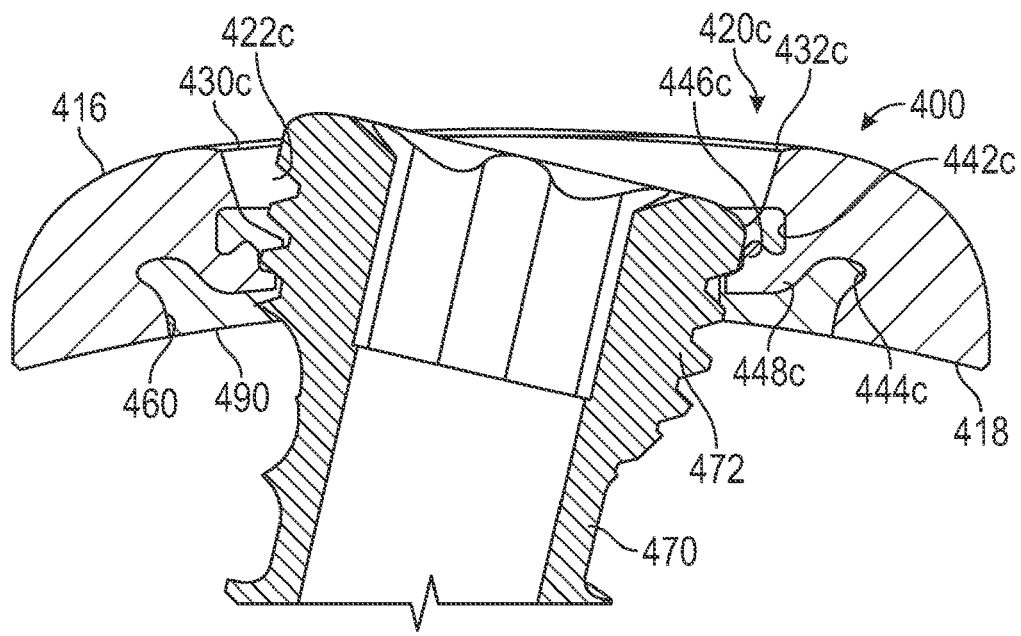
FIG. 11 is a sectional view of the bone plate illustrated in FIG. 7 with a bone screw positioned within an opening of the bone plate. The bone screw extends through the opening at a second angle relative to the central axis of the opening.

Main body 410 defines first 446c and second 448c circumferential projections that are disposed between the upper circumferential recess 442c and lower circumferential recess 444c. In this example, first and second projections that are identical to first 446c and second 448c projections are disposed around each of the other passageways 420a, 420b, 420d, 420e, 420f defined by the main body 410, but are not visible in the drawings. As best illustrated in FIGS. 10 and 11, the inclusion and structural arrangement of first 446c and second 448c projections accommodates the thread 472 of a bone screw 470 disposed through the passageway 420c at multiple angles relative to the central axis of the passageway 420c, such as a coaxial arrangement illustrated in FIG. 10 and an arrangement in which the bone screw 470 is disposed through the passageway 420c at an angle to the central axis of the passageway 420c, as illustrated in FIG. 11. The inclusion and structural arrangement of first 446c and second 448c projections also provides a structure against which the support member 490 can be urged during insertion of the bone screw 470.

As indicated above, support member 490 defines a circumferential wall 422a, 422b, 422c, 422d, 422e, 422f for each passageway 420a, 420b, 420c, 420d, 420e, 420f of the plurality of passageways 420. As best illustrated in FIGS. 8 and 9, the first 446c and second 448c projections are disposed entirely within the support member 490. This structural arrangement allows the thread 472 of a bone screw 470 to extend into the support member when the bone screw 470 is disposed through the passageway 420c, as illustrated in FIGS. 10 and 11. The material is the support member 490 is relatively softer than the material of the main body 410, allowing the support member 490 to be disrupted upon entry of the thread 472. This structural arrangement and composition of the circumferential wall 422c, along with the presence and structural arrangement of the first 446c and second 448c projections, provides for desirable engagement with the thread 472 of a bone screw 470. In one particular example, the second projection disposed around each passageway comprises a circumferential thread itself, which is considered particularly advantageous at least because it further enhances the engagement of a bone screw passed through the passageway.

It is noted that, while not illustrated in FIGS. 7, 8, 9, 10, and 11 does not include a porous portion, bone plate 400 can include one or more porous portions, as described in detail above in connections with example bone plate 100, 200, 300, and 300', for example.

The porous portion in a bone plate according to a particular embodiment can have any suitable dimensions, and a skilled artisan will be able to select appropriate dimensions for a porous portion in a bone plate according to a particular embodiment based on various considerations, including the function of the porous portion. For example, in embodiments in which the porous portion forms a portion of the circumferential wall bounding a screw passageway and is to deform in response to a screw being driven through the passageway, the inventors have determined that a porous portion having a thickness of between about 1 mm and 2 mm is suitable for a passageway having an inner diameter of 4 mm. In embodiments in which the porous portion forms a boundary for a cavity into which a support member is to be formed, such as by injection molding, the inventors have determined that a porous portion having a thickness of between about 0.5 mm and 1 mm is suitable.

Bone plates according to embodiments can be made from any material suitable for use in medical devices intended for orthopedic use, including use as a long-term implant. Examples of suitable materials include metals, metal alloys, and polymeric materials. Inclusion of a porous portion is critical to achieving the desired properties of the inventive bone plates. Accordingly, use of a material that enables formation of a porous portion using appropriate techniques is appropriate. Examples of suitable materials for which appropriate porous portions can be formed using conventional techniques, such as 3D printing, include, but are not limited to, Titanium, Magnesium, and other suitable materials. Examples of suitable metal alloys include stainless steel (316L), cobalt alloys, pure titanium, titanium alloys, magnesium alloys, molybdenum alloys, zirconium alloys, Ti6Al4V, 316 LVM, 1.4441Ti-13Nb-13Zr, Ti-12Mo-6Zr-2Fe, Ti-15Mo-5Zr-3Al, Ti15Mo, Ti-35Nb-7Zr-5Ta and Ti-29Nb-13Ta-4.6Zr Ti-6Al-7Nb and Ti-15Sn-4Nb-2Ta-0.2Pd Co—Cr—Mo alloys.

Non-metal materials are also considered suitable for use in bone plates according to embodiments, both as a main body component and, if included, as a support member component. Examples of suitable non-metal materials include polymeric materials, including plastic metals currently considered suitable for use in medical devices, carbon fiber, polyaryletherketone (PAEK), polyether ether ketone (PEEK), PEEK (90G, 450G, 12, 14), Polyamid, PA66, carbon fiber reinforced polyaryletherketone (CFR PAEK), polyethere ketone ketone (PEKK), carbon fiber reinforced polyether ketone ketone (CFR PEKK), carbon fiber reinforced polyether ether ketone (CFR PEEK), CFR PEEK (90G CA30, 90G CA20, 450G CA30, 450G CA20, 12 CF20, 12 CF30, 14 CF30, 14 CF20), Polyamid CFR, PA66 CFR, and any other materials considered suitable for a bone plate. The inventors have determined that, for embodiments in which the support member includes carbon fiber, it is considered advantageous to include carbon fiber in the material of the support member at an amount that represents a balance between the desirable strength carbon fiber provides and any offsets it contributes to the contourability of the bone plate due to the brittleness of the material. For plates that include a support member comprising carbon fiber reinforced polyether ether ketone (CFR PEEK), it is considered advantageous to include carbon fiber in PEEK at an amount that is less than 5% on a volume basis. It is also considered advantageous to include carbon fiber in PEEK at an amount that is less than 2.5% on a volume basis. It is also considered advantageous to include carbon fiber in PEEK at an amount that is less than 1% on a volume basis. It is also considered advantageous to include carbon fiber in PEEK at an amount that is less than 0.1% on a volume basis. It is also considered advantageous to include carbon fiber in PEEK at an amount that is less than 0.01% on a volume basis.

Figure 12:
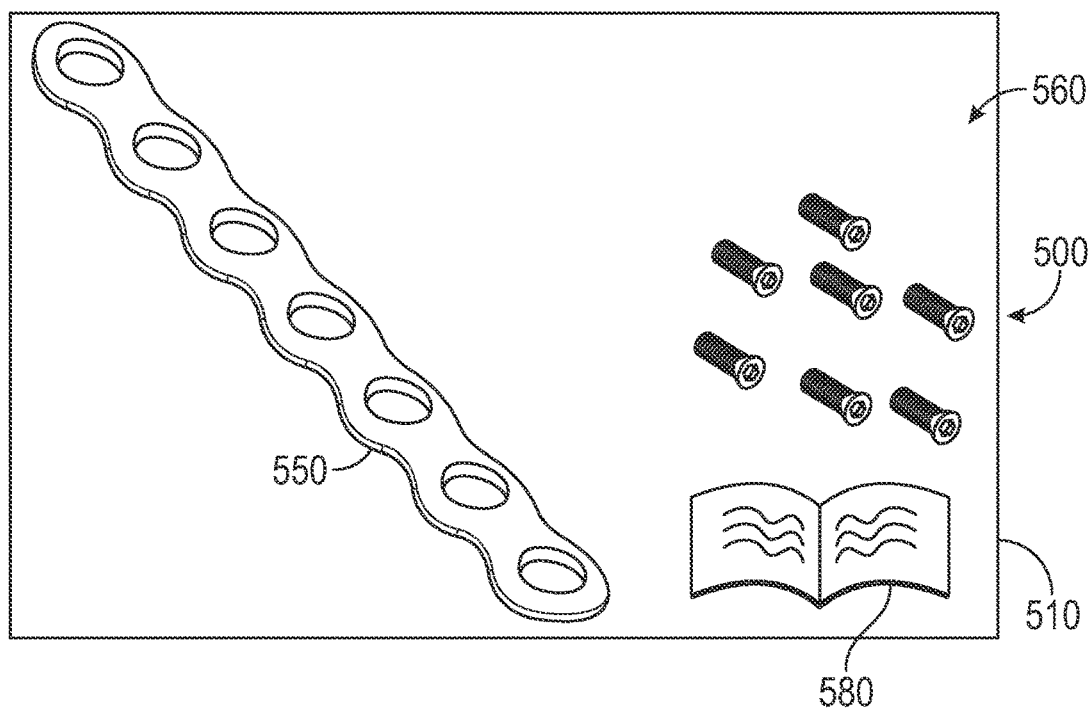
FIG. 12 is a schematic representation of an example bone plate system.

FIG. 12 illustrates an example bone plate system 500. The bone plate system 500 includes a bone plate 550 according to an embodiment, such as the examples described and illustrated herein, and a plurality of bone screws 560. The plurality of bone screws 560 includes a number of bone screws that is at least the same as the number of passageways in the bone plate 550. Also, each bone screw of the plurality of bone screws 560 is adapted to be disposed in one of the passageways of the bone plate 550. The bone plate 550 and the plurality of bone screws 560 can be disposed within or on a container 510. One or more documents 580 containing instructions for using the bone plate 550 and plurality of bone screws 560 together can be included in the container 510.

Figure 13:
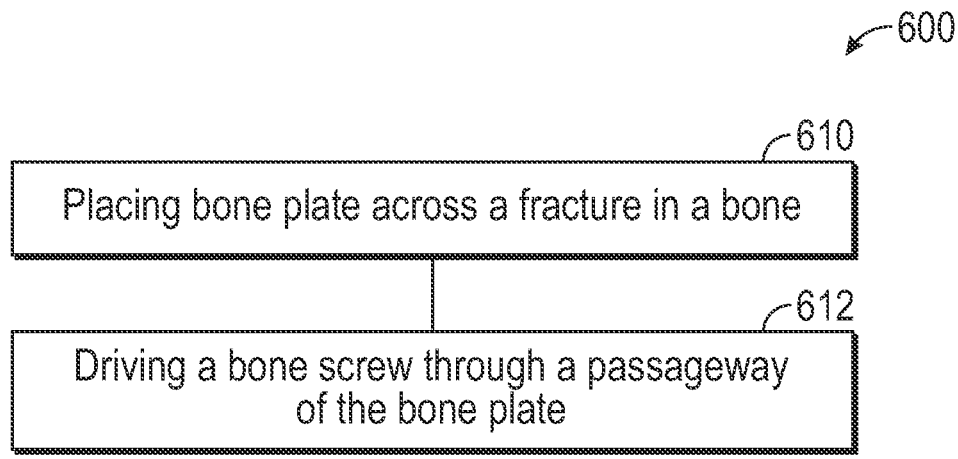
FIG. 13 is a flowchart representation of an example method of treatment.

FIG. 13 is a flowchart representation of an example method of treatment 600. The method 600 is suitable for treatment of a bone fracture. A first step 610 comprises placing a bone plate according to an embodiment across a fracture in a bone such that the lower surface of the bone plate is in contact with the bone. A second step 612 comprises driving a bone screw through a passageway of the bone plate such that the thread of the bone screw deforms the porous portion of the bone plate that comprises a portion of the circumferential wall of the passageway to form a mating thread in the circumferential wall. The second step can be repeated a suitable number of times until a bone screw is driven through each passageway of the bone plate and into the bone.

Figure 14:
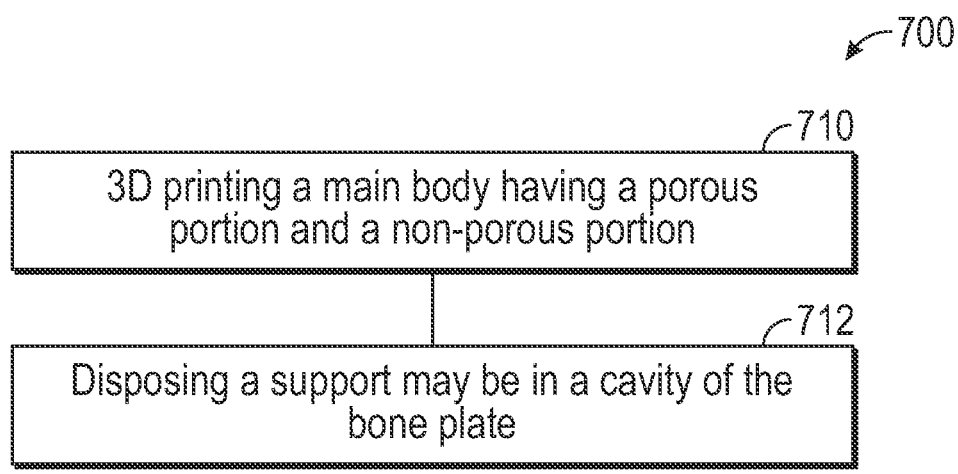
FIG. 14 is a flowchart representation of an example method of manufacturing a bone plate.

FIG. 14 is a flowchart representation of an example method of manufacturing a bone plate 700. A first step 710 comprising 3D printing a main body having a porous portion and a non-porous portion such that the main body defines a plurality of passageways, each of which is bounded at least partially by the porous portion, and a cavity. A second step 712 comprises disposing a support member in the cavity. In one example, the second step 712 is accomplished by injection molding the support member into the cavity such that the polymeric material of the support member extends into the passageways of the porous portion of the main body that bounds each of the passageways. In another example, the second step 712 is accomplished by 3D printing the support member onto the main body such that the support member abuts the porous portion of the main body that bounds each of the passageways. In this example, the support member can be formed to include its own porous portion, such as a porous portion that forms a part of the lower surface of the bone plate that will contact the bone when placed across a fracture in the bone. In another example, the second step 712 is accomplished by 3D printing the support member simultaneously with the 3D printing of the main body. In this example, the support member can be formed to include its own porous portion, such as a porous portion that forms a part of the lower surface of the bone plate that will contact the bone when placed across a fracture in the bone.

Figure 15:
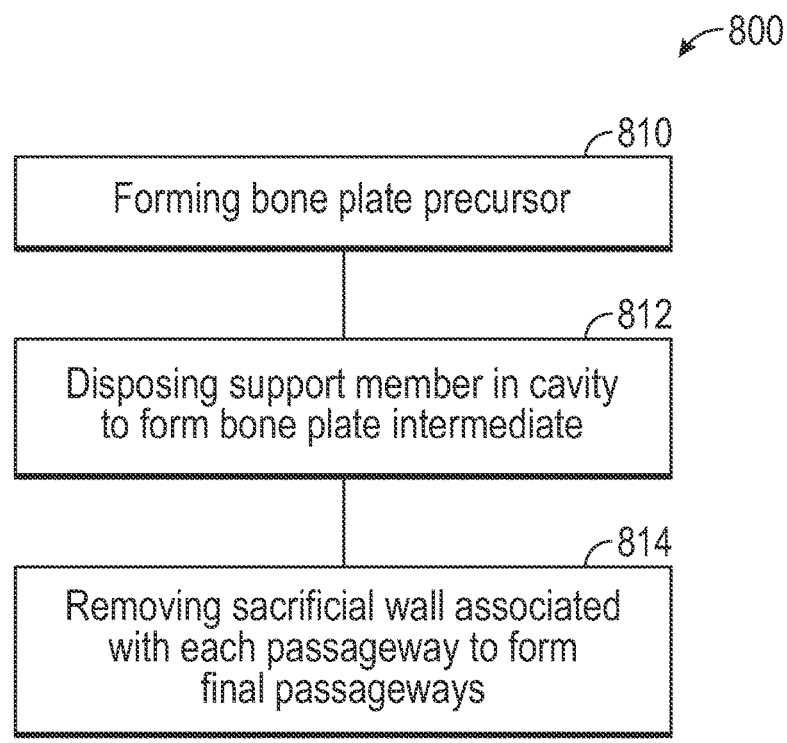
FIG. 15 is a flowchart representation of another example method of manufacturing a bone plate.
Figure 16:
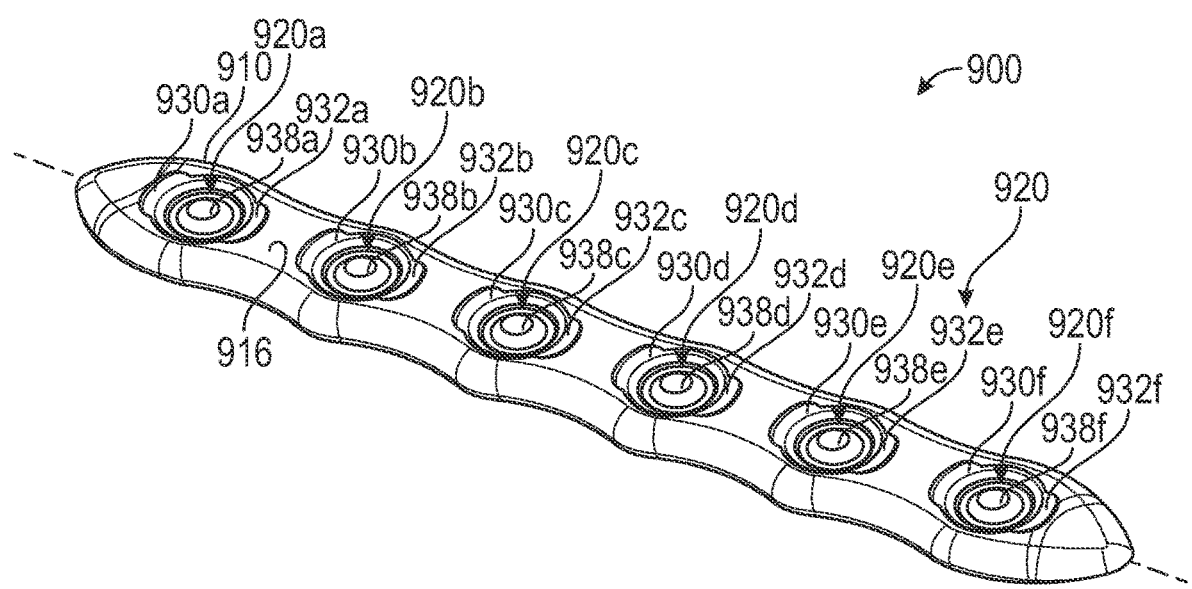
FIG. 16 is a perspective view of a bone plate precursor useful in performance of the method of manufacturing a bone plate illustrated in FIG. 15.

FIG. 15 is a flowchart representation of another example method of manufacturing a bone plate 800. A first step 810 comprises forming a bone plate precursor that includes a main body that defines a plurality of passageways, each of which is blocked by a sacrificial wall, and a cavity. FIG. 16 illustrates an example bone plate precursor 900 formed by performance of step 810. The bone plate precursor 900 includes a plurality of passageways 920, each passageway 920a, 920b, 920c, 920d, 920e, 920f of the plurality of passageways 920 is blocked by a sacrificial wall 938a, 938b, 938c, 938d, 938e, 938f. In one example, the first step 810 is accomplished by 3D printing the bone plate precursor 900. In one particularly advantageous method, the first step is performed such that the bone plate precursor 900 is formed to have a pair of depressions 930a, 932a, 930b, 932b, 930c, 932c, 930d, 932d, 930e, 932e, 930f, 932f formed in an upper surface 916 of the main body 910 adjacent to each passageway 920a, 920b, 920c, 920d, 920e, 920f of the plurality of passageways 920.

Figure 17:
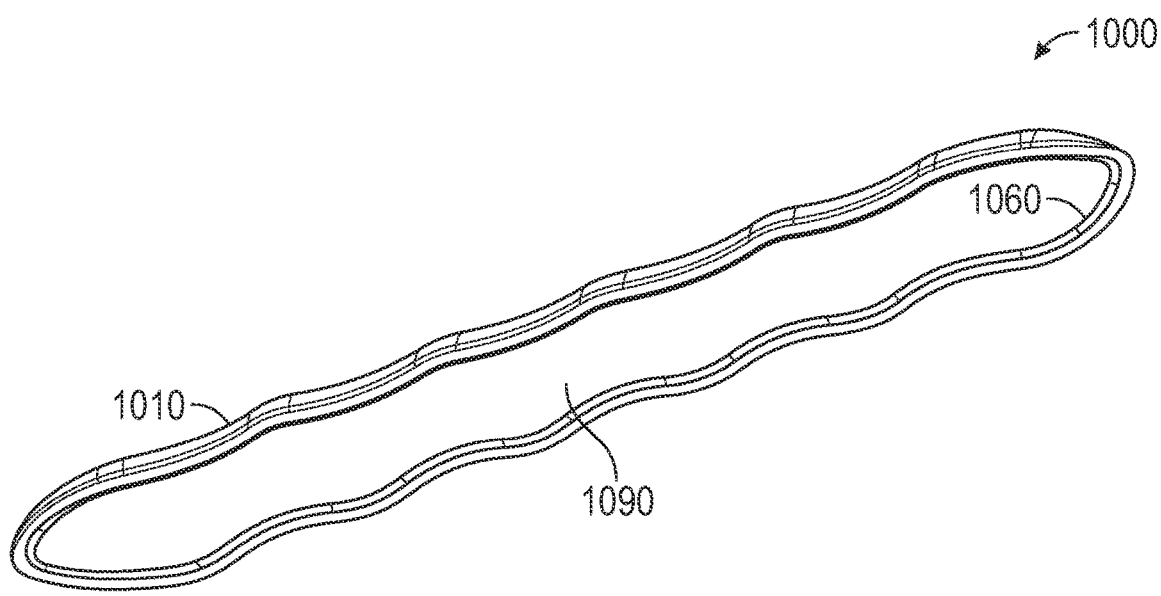
FIG. 17 is a perspective view of a bone plate intermediate formed during performance of the method of manufacturing a bone plate illustrated in FIG. 15.

A second step 812 comprises disposing a support member in the cavity of the bone plate precursor to form a bone plate intermediate that includes a main body that defines a plurality of passageways, each of which is blocked by a sacrificial wall, and a cavity, and a support member disposed within the cavity such that the support member abuts each of the sacrificial walls. FIG. 17 illustrates an example bone plate intermediate 1000 formed by performance of step 812. The bone plate intermediate 1000 includes a main body 1010 that defines a plurality of passageways (not visible in the figure), each passageway of which is blocked by a sacrificial wall (not visible in the figure), and a cavity 1060, and a support member 1090 disposed within the cavity 1060 such that the support member 1090 abuts each of the sacrificial walls. In one example, the second step 812 is accomplished by injection molding the support member 1090 into the cavity 1060 of a bone plate precursor, such as bone plate precursor 900. In another example, the second step 812 is accomplished by 3D printing the support member onto the bone plate precursor. In another example, the second step 812 is accomplished by 3D printing the bone plate precursor simultaneously with the 3D printing of the support member.

Figure 18:
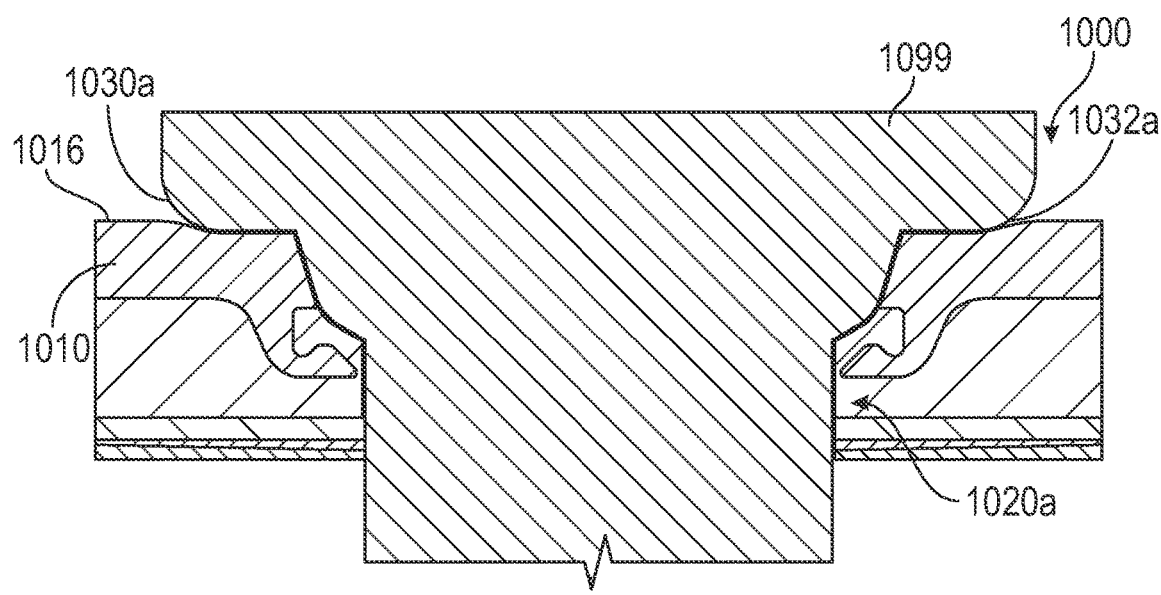
FIG. 18 is a sectional view of the bone plate intermediate during performance of a step of the method of manufacturing a bone plate illustrated in FIG. 15.

A third step 814 comprises removing the sacrificial wall associated with each passageway of the plurality of passageways in the bone plate intermediate to form final passageways that extend through the main body and the support member. In one example, this step 814 is accomplished by drilling through the sacrificial wall and the support member in a bone plate intermediate, such as bone plate intermediate 1000. FIG. 18 illustrates performance of particularly advantageous example of this step 814. In this example, drilling is performed on each passageway 1020a, sequentially or concurrently, until a portion of the drill head 1099 contacts a pair of depressions 1030a, 1032a formed in an upper surface 1016 of the main body 1010 of a bone plate intermediate 1000 adjacent to each passageway 1020a of the plurality of passageways. Step 814 is completed once all sacrificial walls have been removed, providing a finished bone plate. Additional processing steps can be included, such as application of coatings, polishing, and the like.

The foregoing detailed description refers to various example bone plates, bone plate systems, methods of treatment, and methods of manufacturing a bone plate. The description and appended drawings illustrating the described bone plates, bone plate systems, methods of treatment, and methods of manufacturing a bone plate are intended only to provide examples and not to limit the scope of the claims in any manner.

We claim:

1. A bone plate, comprising:
a main body formed of a first material and having a first surface and a second surface opposite the first surface, the main body defining a plurality of main body openings, a plurality of main body circumferential walls, and a cavity that is continuous with the plurality of main body openings, each main body circumferential wall bounding a main body opening of the plurality of main body openings and defining a first circumferential recess and a second circumferential recess disposed around each main body opening of the plurality of main body openings; and
a support member formed of a second, different material and disposed in the cavity of the main body, the support member defining a plurality of support member openings and a plurality of support member circumferential walls, each support member circumferential wall bounding a support member opening of the plurality of support member openings, a portion of the support member disposed in the first circumferential recess and the second circumferential recess of each main body opening of the plurality of main body openings;
wherein each main body opening of the plurality of main body openings is coaxial with a support member opening of the plurality of support member openings to form a passageway partially bounded by one of the plurality of main body circumferential walls and one of the plurality of support member circumferential walls.

2. The bone plate of claim 1, wherein each passageway has an inner diameter; and
wherein one of the plurality of support member circumferential walls defines the inner diameter of each passageway.

3. The bone plate of claim 1, wherein the main body defines first and second circumferential projections disposed around each main body opening of the plurality of main body openings.

4. The bone plate of claim 3, wherein each of the first and second circumferential projections are disposed between the first circumferential recess and the second circumferential recess of one of the plurality of main body openings.

5. The bone plate of claim 4, wherein the first and second circumferential projections disposed around each main body opening of the plurality of main body openings are disposed entirely within the support member.

6. The bone plate of claim 1, wherein the first material comprises a metal.

7. The bone fixation plate of claim 6, wherein the first material comprises one or more of Titanium, Magnesium, Ti6Al4V, 316 LVM, 1.4441Ti-13Nb-13Zr, Ti-12Mo-6Zr-2Fe, Ti-15Mo-5Zr-3Al, Ti-15Mo, Ti-35Nb-7Zr-5Ta and Ti-29Nb-13Ta-4.6Zr Ti-6Al-7Nb and Ti-15Sn-4Nb-2Ta-0.2Pd Co—Cr—Mo alloys.

8. The bone plate of claim 1, wherein the second material comprises a polymeric material.

9. The bone fixation plate of claim 8, wherein the second material comprises one or more of PAEK, CFR PAEK, PEKK, CFR PEKK, PEEK, CFR-PEEK, PEEK (90G, 450G, I2, I4), Polyamid, and PA66.

10. The bone fixation plate of claim 1, wherein the first material comprises a Titanium alloy and the second material comprises PEEK.

11. The bone fixation plate of claim 1, wherein the support member comprises an overmolded structure formed on the main body.

12. A bone plate, comprising:
a main body formed of a first material and having a first surface and a second surface opposite the first surface, the main body defining a first main body circumferential wall bounding a first main body opening, a second main body circumferential wall bounding a second main body opening, and a cavity that is continuous with the first and second main body openings; and
a support member formed of a second, different material and disposed in the cavity of the main body, the support member defining a first support member circumferential wall bounding a first support member opening that is coaxial with the first main body opening and a second support member circumferential wall bounding a second support member opening that is coaxial with the second main body opening.

13. The bone plate of claim 12, wherein the first main body opening has a first main body inner diameter, the second main body opening has a second main body inner diameter, the first support member opening has a first support member inner diameter that is less than the first main body opening inner diameter, and the second support member opening has a second support member inner diameter that is less than the second main body opening inner diameter.

14. The bone plate of claim 12, wherein the first material comprises a metal.

15. The bone fixation plate of claim 14, wherein the first material comprises one or more of Titanium, Magnesium, Ti6Al4V, 316 LVM, 1.4441Ti-13Nb-13Zr, Ti-12Mo-6Zr-2Fe, Ti-15Mo-5Zr-3Al, Ti-15Mo, Ti-35Nb-7Zr-5Ta and Ti-29Nb-13Ta-4.6Zr Ti-6Al-7Nb and Ti-15Sn-4Nb-2Ta-0.2Pd Co—Cr—Mo alloys.

16. The bone plate of claim 12, wherein the second, different material comprises a polymeric material.

17. The bone plate of claim 16, wherein the second, different material comprises one or more of PAEK, CFR PAEK, PEKK, CFR PEKK, PEEK, CFR-PEEK, PEEK (90G, 450G, 12, 14), Polyamid, and PA66.

18. The bone plate of claim 17, wherein the first material comprises a Titanium alloy and the second material comprises PEEK.

19. A bone plate, comprising:
a main body comprising a metal and having a first surface and a second surface opposite the first surface, the main body defining a first main body circumferential wall bounding a first main body opening, a second main body circumferential wall bounding a second main body opening, a first and second circumferential recesses disposed around the first main body opening, third and fourth circumferential recesses disposed around the second main body opening, first and second circumferential projections disposed between the first and second circumferential recesses, third and fourth circumferential projections disposed between the third and fourth circumferential recesses, and a cavity that is continuous with the first and second main body openings; and
a support member comprising a polymeric material and disposed in the cavity of the main body and the first, second, third, and fourth circumferential recesses, the support member defining a first support member circumferential wall bounding a first support member opening that is coaxial with the first main body opening and a second support member circumferential wall bounding a second support member opening that is coaxial with the second main body opening.

20. The bone plate of claim 19, wherein the metal comprises a Titanium alloy and the polymeric material comprises PEEK.

* * * * *

UNITED STATES PATENT AND TRADEMARK OFFICE
CERTIFICATE OF CORRECTION

PATENT NO. : 12,193,717 B2
APPLICATION NO. : 17/716479
DATED : January 14, 2025
INVENTOR(S) : Axel Cremer, Garret Mauldin and Anna Zastrozna Page 1 of 1

It is certified that error appears in the above-identified patent and that said Letters Patent is hereby corrected as shown below:

In the Claims

Column 13, Claim 7, Line 17, from: "Ti6A14V,"
To: --Ti6Al4V,--

Column 13, Claim 7, Line 18, from: "Ti-15Mo-5Zr-3A1,"
To: --Ti-15Mo-5Zr-3Al, --

Column 13, Claim 7, Line 19, from: "Ti-6A1-7Nb,"
To: --Ti-6Al-7Nb,--

Column 14, Claim 15, Line 10, from: "Ti6A14V,"
To: --Ti6Al4V,--

Column 14, Claim 15, Line 11, from: "Ti-15Mo-5Zr-3A1,"
To: --Ti-15Mo-5Zr-3Al,--

Column 14, Claim 15, Line 12, from: "Ti-6A1-7Nb,"
To: --Ti-6Al-7Nb,--

Column 14, Claim 17, Line 19, from: "(90G, 450G, 12, 14),"
To: --(90G, 450G, I2, I4),--

Signed and Sealed this
Eighteenth Day of March, 2025

Coke Morgan Stewart
*Acting Director of the United States Patent and Trademark Office*